United States Patent [19]

Weston et al.

[11] Patent Number: 5,246,851

[45] Date of Patent: Sep. 21, 1993

[54] MONOCLONAL ANTIBODY SPECIFIC FOR A 14KD PROTEIN OBTAINED FROM N GONORROEAE

[76] Inventors: Peter D. Weston; Susan G. Hadfield; Ann Lane, all of The Wellcome Research Laboratories, Langley Ct., Beckenham Kent BR3 3BS, England

[21] Appl. No.: 580,915

[22] Filed: Sep. 12, 1990

[30] Foreign Application Priority Data

Sep. 20, 1989 [GB] United Kingdom .................. 8921227

[51] Int. Cl.$^5$ .......................... C12N 5/00; C07K 15/28
[52] U.S. Cl. ............................. 435/240.27; 435/7.36; 530/388.4; 530/825
[58] Field of Search ................ 435/7.36, 70.21, 240.27, 435/871; 530/387

[56] References Cited

U.S. PATENT DOCUMENTS 4,755,459  7/1988  Pearson et al. .................... 435/7.36

FOREIGN PATENT DOCUMENTS 1220147  5/1987  Canada .
2172704  9/1986  United Kingdom .

OTHER PUBLICATIONS

Klugman et al. Infection and Immunity, 57(7):2066–2071.
Copley et al, "The Production and Characterization of Monoclond Antibodies Against The Protein III of *Neisseria Gonorrhoeae*" J. Gen Microbiol. 134: 1005–1008 (1988).
*Infection and Immunity*, Nov. 1982, pp. 462–470, vol. 38, No. 2, Sandstrom et al, "Serology of Neisseria Gonorrhoeae . . . ".
*Infection and Immunity*, Dec. 1981, pp. 804–816, vol. 34, No. 3, Swanson, "Surface-Exposed Protein Antigens of the Gonococcal Outer . . . ".

*Primary Examiner*—Esther L. Kepplinger
*Assistant Examiner*—Carol E. Bidwell
*Attorney, Agent, or Firm*—Nixon & Vanderhye

[57] ABSTRACT

A monoclonal antibody, specific for *N. gonorrhoeae*, specifically binds to a protein which is obtained from *N. gonorrhoeae*, which has a molecular weight of about 14 kD as determined by SDS-PAGE and which specifically binds to antibody secreted by hybridoma NG 28 (ECACC 89 07 19 01).

4 Claims, No Drawings

MONOCLONAL ANTIBODY SPECIFIC FOR A 14KD PROTEIN OBTAINED FROM N GONORROEAE

This invention relates to antibodies and proteins useful in the detection of *Neisseria gonorrhoeae*.

Diagnosis of clinical gonorrhoea is complicated by two factors. First, there are several serotypes of *N. gonorrhoeae*. Tests which rely on detection of a serotype-specific epitope are therefore unreliable. Second, closely related to *N. gonorrhoeae* is *N. meningitidis*. In conventional assay procedures *N. meningitidis* commonly cross-reacts with *N. gonorrhoeae*. A test for *N. gonorrhoeae* must be capable of adequately distinguishing between the two species.

GB-A-2172704 describes a proteinaceous material with a molecular weight of about 20 kD which is isolated from a sodium cholate extract of outer membrane vesicles of *N. gonorrhoeae* strain BS4 (NCTC 11922). The use of this material to prepare hybridomas is disclosed. CA-A-1220147 describes the detection of *N. gonorrhoeae* using monoclonal antibody to *N. gonorrhoeae* antigens, especially to R-core lipopolysaccharide.

A monoclonal antibody has now surprisingly been found which reacts with a *N. gonorrhoeae*-specific epitope occurring in all *N. gonorrhoeae* serotypes tested. A protein which presents this epitope has been isolated. This protein may be contrasted with the well known protein I or major outer membrane protein of *N. gonorrhoeae* which varies between strains and serves to define different serotypes within the species (Sandstrom E. G. et al, Infect. Immun. (1982) 38, 462). No epitope has been defined on protein I which is present in all serotypes of *N. gonorrhoeae* but not in *N. meningitidis* serotypes.

Copley and McFarlane (J. Gen. Microbiol. (1988) 134, 1005) have reported a monoclonal antibody to gonococcal protein III which reacts with all *N. gonorrhoeae* isolates tested. The molecular weight of protein III is however approximately 37,000 (Swanson J., Infect. Immun. (1981) 34, 804-816). This serves to distinguish that protein from the protein which we have isolated and which has a molecular weight of approximately 14,000.

Accordingly, the present invention provides a monoclonal antibody which is specific for *N. gonorrhoeae* and which is capable of binding to a protein which is obtainable from *N. gonorrhoeae*,
has a molecular weight of about 14 kD as determined by sodium dodecyl sulphate-polyacrylamide gel electrophoresis (SDS-PAGE), and
binds to antibody secreted by hybridoma NG 28.

The monoclonal antibody of the invention has no cross-reactivity with *N. meningitidis*.

Immortalised cell lines such as hybridoma NG 28 which secrete such monoclonal antibody and the protein itself also form part of the invention. Hybridoma NG 28 was deposited at the European Collection of Animal Cell Cultures, Porton Down, GB on 19 July 1989 under accession no. ECACC 89071901.

Monoclonal antibodies according to the present invention are specific for an epitope on the protein of the invention. The protein can be obtained from a strain of *N. gonorrhoeae* by extracting the *N. gonorrhoeae* organisms such as to release the said protein, contacting the extract with a monoclonal antibody according to the invention and recovering the desired protein which will thus have become bound to the monoclonal antibody. The protein of the invention can thus be obtained in substantially pure form. The monoclonal antibody may in particular be that secreted by hybridoma NG 28.

Extraction of the *N. gonorrhoeae* may be achieved by using a detergent, preferably in association with a buffer. The detergent may be a non-ionic or zwitterionic detergent. Of the detergents tested, non-ionic detergents such as Tween ® 20, Tween 80, Triton ® X100, Lubrol ® WX and Lubrol PX were particularly effective. It was also found that the zwitterionic detergent 3-(3-cholamidopropyl)-dimethylammonio-1-propane sulphonate (CHAPS) was effective. At a final level of 0.01 w/v the above detergents did not solubilise the protein of the invention but at 0.1 w/v the protein was found to be released.

The *N. gonorrhoeae* may be present in an aqueous buffer of a pH of from 6 to 8, for example about pH 7. A sodium phosphate buffer with a pH of 7.4 can be employed. A suitable procedure is to suspend the *N. gonorrhoeae* bacteria overnight in 66 mM sodium phosphate buffer pH 7.4 containing 0.1% CHAPS w/v. The detergent releases the protein of the invention from the bacterial cells. Residual bacterial debris can be removed by centrifugation. The supernatant can be filtered through a 0.45 μm Sartorius ® membrane filter.

The extract is then brought into contact with monoclonal antibody specific for the protein of the invention such as the antibody secreted by hybridoma NG 28. Typically the monoclonal antibody is attached to a solid support in an immunoabsorbant column. A finely divided solid support is typically poured into a column. The extract is introduced onto the column and the protein which has bound to the antibody is subsequently eluted.

The protein has the following properties after purification in this manner:

Spectrophotometric data

A 1 mg/ml solution of the immunoabsorbant-purified protein gave an $OD^{1cm}_{280nm} = 3.04$.

Blocked N-terminal amino acid

Dansyl N-terminal analysis showed a spot corresponding to the dansyl derivative of the amino group of lysine but no other spots were visible. This suggested that the N-terminal amino acid of the protein was blocked.

Amino acid analysis

The protein purified on the immunoabsorbant column was oxidised with periodic acid and duplicate samples hydrolysed with 5.8N HCl containing 0.1% phenol w/v in vials sealed under vacuum for 24, 48 and 72 hours at 110° C. The samples were analysed in a Biotronic 5001 amino acid analyser supplied by Biotech Instruments, Luton, GB using an ion exchange column and ninhydrin detection based on the method described by Spackman et al, Anal. Chem. 30, 1190-1206, 1959.

|  | Precise data | Rounded figure |
| --- | --- | --- |
| Cysteic acid | none detected |  |
| Aspartic acid | 9.49 | 9 |
| Methionine sulphate | 0.49 | 1 |
| Threonine* | 4.85 | 5 |
| Serine* | 16.05 | 16 |
| Glutamic acid | 19.53 | 20 |

-continued

| | Precise data | Rounded figure |
|---|---|---|
| Proline | 2.66 | 3 |
| Glycine | 19.59 | 19 |
| Alanine | 17.82 | 18 |
| Valine | 9.70 | 10 |
| Isoleucine | 5.29 | 5 |
| Leucine | 5.38 | 5 |
| Tyrosine | none detected | 0 |
| Phenylalanine | 1.86 | 2 |
| Glucosamine | none detected | 0 |
| Galactosamine | none detected | 0 |
| Histidine | 1.46 | 1 |
| Lysine | 8.33 | 8 |
| Arginine | 2.04 | 2 |
| Tryptophan+ | 8.7 | 9 |
| | Total = | 133 |

*Corrected to zero time for losses during hydrolysis.
+Calculated from the observed absorbance and the known extinction coefficient at 280 nm.

Calculated molecular weight of the protein = 13,892. The protein is unusual in having no detectable tyrosine and it is probably not glycosylated since no amino sugars were found.

Peptide sequences

Immunoabsorbant-purified protein (5 nmole) was treated with cyanogen bromide, then digested with trypsin and the peptides separated on a Vydac ® C18 reverse phase column at 30° C. packed with 30 nm pore, 10 μm particles. Peptide peaks with significantly large areas were chosen and after dansyl analysis three were taken for sequencing. Using a pulsed gas liquid phase sequencer the following sequences according to the one letter code (Eur. J Biochem. 138, 9-37, 1984) were deduced from the data:

| Peptide No. | Sequence |
|---|---|
| CTG-19 | EGVSKAEAEDIQK |
| CTG-11 | AEAEDIQK |
| CTG-17 | DIVDGAPK |

SDS electrophoresis

When the immunoabsorbant-purified protein was run on 15% acrylamide gel it ran as a single band behind the dye front just faster than the lowest molecular weight marker which was hen egg white lysosyme, molecular weight 14,400. These data suggested that the protein was slightly smaller than hen egg white lysosyme and had a molecular weight of about 14 kD.

Immunoblotting

Extracts were made of pilated and non-pilated *N. gonorrhoeae* colonies. The extracts were run in SDS electrophoresis and blotted onto nitrocellulose. Using peroxidase-labelled NG28 monoclonal antibody a single band was seen running just behind the dye front. Both pilated and non-pilated strains gave the same result suggesting that the protein is not a constituent of pili. Pilin subunits have a molecular weight of 18,000-22,000 (Hagblom, P. et al. Nature (1985) 315, 156).

Properties of rabbit antisera to the purified specific protein

Sera from 2 rabbits immunised with the immunoabsorbent-purified protein were diluted, with 150 mM saline, 1/400 then doubling dilutions to 1/51200. Then aliquots (75 μl) were added to wells on microtitre plates coated either with formalised *N. meningitidis* or with formalised *N. gonorrhoeae*. After incubation for 1 hour at 37° C. the plates were washed repeatedly with 0.05% Tween (Trade Mark) saline and aliquots (75 μl) of horseradish peroxidase-labelled swine (anti-rabbit) IgG 1/2000 in pH 8.2 100 mM glycine buffered saline were added. After a further incubation for 1 hour at 37° C. the plates were washed again and the bound peroxidase detected with tetramethylbenzidine/$H_2O_2$ substrate. The titres of the antisera on the *N. gonorrhoeae* plates were very similar to those on the *N. meningitidis* plates. This suggested that the immunising antigen contained epitopes common to *N. gonorrhoeae* and *N. meningitidis*.

Serum from one of the immunised rabbits was passed slowly down a column of CN.Br Sepharose ® linked to formalised *N. meningitidis*. When the eluted fractions were tested on coated microtitre plates as before there was a differential drop in titre. For example with an early eluted fraction the anti-*N. gonorrhoeae* titre dropped 8 fold whilst the anti-*N. meningitidis* titre dropped 50 fold. This suggested that the serum contained some antibodies which react with epitopes shared by *N. meningitidis* and *N. gonnorhoeae* and some which may react with *N. gonorrhoeae*-specific epitopes.

The protein of the invention can be used to prepare an immortalised cell line which secretes monoclonal antibody according to the invention. This may be achieved by a process which comprises immunising an animal with the protein, obtaining from the immunised animal cells which secrete antibody specific for the protein, fusing the said cells with cells of an immortalising cell line and screening the resulting immortalised cell lines for an immortalised cell line which secretes monoclonal antibody of the invention.

Typically, a non-human mammalian host such as a mouse or rat is inoculated with the protein of the invention. After sufficient time has elapsed to enable the host to mount an antibody response to the protein, antibody-producing cells are removed. The spleen may be removed, for example. The antibody-producing cells such as the splenocytes are fused with cells of an immortalising cell line such as a myeloma cell line e.g. of a mouse or rat. The resulting fusions are screened. An immortalised cell line, such as a hybridoma, secreting monoclonal antibody specific for the protein of the invention is thereby selected.

The resulting immortalised cell line can be used to obtain monoclonal antibody specific for the protein. Monoclonal antibody according to the invention is prepared by a process comprising:

(a) culturing an immortalised cell line which secretes the said monoclonal antibody: and (b) isolating the said antibody thus produced.

The cell line may be hybridoma NG 28. Progeny of clones producing the desired antibody can be grown. Step (a) may be conducted in vitro in suitable culture media in tissue culture flasks or in a hollow fibre tissue culture device for example. Alternatively cells may be cultured in step (a) in vivo. They may be grown in vivo in laboratory animals, for example in laboratory animals, such as mice and rats. Cells of the immortalised cell line may be implanted in a body cavity, such as the abdominal cavity, of the animal and allowed to grow. The resulting monoclonal antibody can be separated from the culture medium or from the body cavity fluid such as the ascites fluid of the animal by techniques such as ammonium sulphate precipitation, ion exchange chromatography, affinity chromatography, high-performance liquid chromatography, etc. The antibody may be, for example IgG, IgM or IgA.

Polyclonal antibody capable of binding to the 14 kD protein of the invention can also be prepared by injecting such protein, typically in substantially pure form, into an animal, typically a non-human mammal such as a mouse, rat, sheep or rabbit, and recovering the antibody thus produced capable of binding to the protein. The protein is typically administered as an injectable formulation comprising also a physiologically acceptable diluent. Adjuvants such as Freund's complete adjuvant (FCA), Freund's incomplete adjuvant (FIA) or aluminium hydroxide may be included in the formulation. The animals are immunised over a suitable period of time. They are bled at appropriate intervals for assay for anti-protein activity. When an appropriate level of activity is reached, the animals are bled. Antibody is extracted and purified e.g. by salt precipitation, affinity chromatography using immobilised protein A or ion exchange or high performance liquid chromatography.

The monoclonal antibody of the invention is used to assay for N. gonorrhoeae. A method of determining N. gonorrhoeae in a sample is provided which uses a monoclonal antibody of the invention. This may be achieved by extracting a sample suspected of containing N. gonorrhoeae such as to release the protein of the invention, if N. gonorrhoeae is present; contacting the extract with the monoclonal antibody; and determining whether the said antibody has bound to any protein of the invention.

The sample suspected of containing N. gonorrhoeae may be assayed by this method. A sample may be a swab from the urethra, cervix, vagina, throat, penis, rectum or eye. Alternatively the sample may be a sweep from a culture of bacteria grown on solid or in liquid media. Extraction typically involves using a detergent to release the protein of the invention from cells of N. gonorrhoeae. Extraction procedures are as described above.

A variety of assay formats may be employed. The monoclonal antibody of the invention can be used to capture selectively onto a solid surface from solution the protein of the invention, to label selectively this protein or both to capture and to label this protein. The antibody also may be used in a variety of homogeneous assay formats in which the protein of the invention is detected in solution with no separation of phases.

The types of assay in which antibody is used to capture the protein from solution involve immobilization of the antibody onto a solid surface. This surface should be capable of being washed. The types of surfaces which may be used include polymers of various types (moulded into microtitre wells; beads; dipsticks; aspiration tips; electrodes; and optical devices), particles (for example latex; stabilized red blood cells (erythrocytes); bacterial or fungal cells; spores; gold or other metallic or metal-containing sols; organic sols; and proteinaceous colloids; with the usual size of the particle being from 0.005 to 5, for example from 0.1 to 5 microns), membranes (for example of nitrocellulose paper; cellulose acetate: chemically-activated membranes such as Millipore Immobilon ® or Pall Biodyne ®; and high porosity/high surface area membranes of an organic or inorganic material).

The attachment of the antibody to the surfaces can be by passive adsorption from a solution of optimum composition which may include surfactants, solvents, salts and/or chaotropes; or by active chemical bonding. Active bonding may be through a variety of reactive or activatable functional groups which may be exposed on the surface (for example condensing agents; active esters, acid halides, anhydrides; amino, hydroxyl, or carboxyl groups; sulphydryl groups; carbonyl groups; diazo groups; unsaturated groups).

After contacting (reacting) the surface bearing the antibody with a test sample, allowing time for reaction and, where necessary, separating or removing the excess of the sample by any of a variety of means (washing, centrifugation, filtration, application of a magnetic field, capillary action), the captured protein of the invention is detected by any means which will give a detectable signal. For example, this may be achieved by use of a labelled molecule, in particular antibody, or particle as described above which will react with the captured protein.

The detectable signal may be optical or radio-active or physico-chemical and may be provided either directly by labelling the molecule or particle, especially antibody, referred to with for example a dye, radiolabel, electroactive species, magnetically resonant species or fluorophore, or indirectly by labelling the molecule or particle with an enzyme itself capable of giving rise to a measurable change of any sort. Alternatively the detectable signal may be due to, for example, agglutination, diffraction effect or birefringent effect occurring if any of the surfaces referred to is in the form of particles.

A preferred assay format is the sandwich assay. A first antibody capable of binding to the protein of the invention captures the protein onto a solid surface and a second antibody capable of binding to the protein of the invention labels the protein. At least one of the first antibody and the second antibody is a monoclonal antibody of the invention. One of the antibodies, for example the first antibody, may be a polyclonal antibody. The polyclonal antibody may have been raised against intact N. gonorrhoeae cells or against the protein of the invention. The capturing and labelling operations may be performed in any order or simultaneously.

Typically the second antibody is labelled with an enzyme such as an alkaline phosphatase or peroxidase. A useful sandwich assay therefore involves contacting an extract of N. gonorrhoeae with enzyme-labelled monoclonal antibody according to the invention, capturing the resulting immune complex onto a solid surface using a polyclonal antibody capable of binding to the protein of the invention, removing any excess labelled antibody and adding a substrate for the enzyme. The presence of the protein of the invention in the original extract and thereby of N. gonorrhoeae in the original sample is thus revealed.

Other formats which may be employed are any of those suitable for immunoassays including 1) agglutination with the monoclonal antibody of the invention adsorbed onto particles of for example polystyrene latex, 2) a conventional enzyme-linked immunoadsorbant assay (ELISA) carried out in microtitre plates, 3) a dipstick ELISA with an antibody-coated dipstick, and 4) sandwich assays using small magnetic particles coated with capture antibody together with the monoclonal antibody labelled either with coloured particles, or particles with the potential of colour development, or with an enzyme or a fluorescent moiety.

The invention also provides test kits suitable for use in determining N. gonorrhoeae. Such kits comprise a monoclonal antibody according to the invention and means for determining whether the said antibody binds to the protein of the invention described above. Specific components of the kits may be as described above. The kits may also comprise one or more additional components selected from controls, buffers, diluents and detergents.

A kit for use in an enzyme-immunoassay typically includes an enzyme-labelled reagent and a substrate for the enzyme. The enzyme may either be bound to the monoclonal antibody of the invention which can bind to the protein of the invention or be bound to polyclonal or monoclonal antibody capable of binding to the monoclonal antibody.

The monoclonal antibody of the invention can also be used to assay for N. gonorrhoeae without first extracting a sample under test. Such a method comprises contacting a sample suspected of containing N. gonorrhoeae with the monoclonal antibody and determining whether the said antibody has bound to any protein according to the invention on the surface of N. gonorrhoeae bacteria.

For this purpose, the antibody of the invention is labelled, for example as described above. The label may be a fluorescent or enzyme label. In the former case, N. gonorrhoeae may be examined under a microscope using a fluorescent labelled antibody. In the latter case, an enzyme immunoassay may be carried out.

The following Examples illustrate the invention.

EXAMPLE 1

Production of Hybridoma NG 28

(a) Immunisation and fusion

Three N. gonorrhoeae strains representative of the W1 sub-class and three representing the W2/3 subclass were separately grown in petri dishes on N. gonorrhoeae selective medium enriched with vitamins in an atmosphere of 5% $CO_2$. Bacteria were harvested and formalised by suspension in 0.25% formal saline and taken to a final $OD^{1cm}{}_{600nm}=0.1$. Suspensions of the six strains were pooled and homogenised with an equal volume of Freund's Incomplete Adjuvant.

Balb/C mice were immunised subcutaneously with 100 μl of antigen suspension and left at least one month before proceeding. Four days before fusion the mice were boosted with a further injection 100 μl intraperitoneally of the formalised suspension of the six bacterial strains mixed with an equal volume of sterile saline. The spleens were removed from the mice. Splenocytes were fused with Non-secreting O myeloma cells of Balb/C origin using polyethylene glycol (PEG) 1540. The resulting hybridomas were isolated and grown up.

(b) Screening procedure

Each hybridoma supernatant was screened to detect antibodies to N. gonorrhoeae and N. meningitidis. For this purpose Nunc (Trade Mark) high binding microtitre plate wells were each coated with 95 μl of formalised bacterial suspension in 50 mM sodium bicarbonate/carbonate buffer pH 9.5. For N. gonorrhoeae, a pool of six strains with equal levels of three representatives of W1 sub-class and three of W2/3 subclass at $OD^{1cm}{}_{600nm}=0.2$ was used. The six strains were the same as those used in Example 1(a). For N. meningitidis, a single strain at $OD^{1cm}{}_{600nm}=0.1$ was employed.

Coating was for 4 h at 37° C., then the plates were shaken out and blocked by filling the wells with 0.5% bovine serum albumin in 100 mM glycine buffer pH 8.2 including 150 mM sodium chloride. Blocking was for at least one hour, then when required the plates were washed with 0.05% Tween 20 in 150 mM sodium chloride and shaken out firmly. Each hybridoma supernatant (70 μl) was pipetted into both a N. gonorrhoeae and a N. meningitidis coated well. The plates were then covered and incubated in a water bath at 37° C. for 1 hour. The contents of the wells were aspirated and the plates washed with 0.05% Tween 20 saline eight times using a Dynawasher (Trade Mark) 2 plate washer.

Anti-(mouse IgG) (70 μl) obtained from rabbit and labelled with horseradish peroxidase was diluted ×4000 in 0.5% bovine serum albumin in saline and added to each well. The incubation was repeated in the water bath at 37° C. for 1 h. The plates were then washed as above and tetramethylbenzidine/$H_2O_2$ substrate (70 μl) added to detect bound peroxidase. After 30 min at room temperature the enzymic reaction was stopped by the addition of 2M sulphuric acid (70 μl). The yellow colour developed in the positive wells was measured using a Behring Elisa Processor 2.

(c) Selection of N. gonorrhoeae specific hybridomas

Hybridoma supernatants which gave a high optical density on the N. gonorrhoeae coated wells and a low optical density on the N. meningitidis coated wells were selected for limited dilution cloning. During the cloning process hybridoma supernatants were repeatedly screened using the N. gonorrhoeae and N. meningitidis coated microtitre plates. Those wells which gave the highest ratio of colour N. gonorrhoeae/N. meningitidis where chosen for continued culture.

A minimum of ten single colony supernatants was screened at each cloning stage and the cell lines were considered monoclonal only when two successive screens had given 100% positive results. From fusions done with 9 mouse spleens a total of 29 monoclonal lines was established and 2 of these showed a particularly high N. gonorrhoeae/N. meningitidis ratio.

(d) Preparation of purified antibody

The monoclonal cell lines were separately inoculated into mice for the preparation of ascitic fluid. IgG was isolated from the ascites using protein A-Sepharose chromatography.

(e) Specificity testing and Identification of particular clones

For specificity testing of the purified IgG, freshly prepared suspensions of live bacteria (100 μl) in 50 mM sodium bicarbonate buffer pH 9.5 were adjusted to $OD^{1cm}{}_{600nm}=0.5$ and coated overnight at 4° C. onto Nunc high binding microtitre plates. The plates were then blocked with bovine serum albumin 0.5% in saline for 1 h at room temperature.

The purified IgG solution was diluted from 2 μg/ml in 10 fold dilutions using 0.5% bovine serum albumin in saline as diluent. Aliquots (100 μl) of the dilutions were applied to the wells coated with bacteria and the plates incubated for 1 hour at 37° C. After washing with 0.05% Tween 20 in 150 mM saline, a horseradish peroxidase-labelled rabbit anti-(mouse IgG) conjugate (100 μl) diluted 1/4000 in 0.5% bovine serum albumin in 50 mM phosphate buffered saline pH 7.0 was added to each well.

The plate was incubated a further 1 hour at 37° C. and then it was washed again with 0.05% Tween 20 in 150 mM saline before adding tetramethylbenzidine/$H_2O_2$ substrate. With mouse IgG from the NG28 cell line at 200 ng/ml all the N. gonorrhoeae strains tested gave a reading >0.95 whilst the *N. meningitidis* strains tested gave a reading <0.17. This clone was thus identified as being of particular interest.

(f) Specificity testing using a peroxidase labelled monoclonal IgG

Further specificity testing using numerous serotypes *N. gonorrhoeae* and serogroups of *N. meningitidis* was done using purified IgG from NG28 labelled directly with horseradish peroxidase. In this test 100 µl dilutions of the peroxidase-labelled antibody from 1/2000 to 1/16000 were incubated with the bacteria-coated plates for 1 hour at 37° C. After washing with 0.05% Tween 20 saline, peroxidase activity was detected immediately with tetramethylbenzidine/$H_2O_2$ substrate as before.

In this instance a 1/8000 dilution of the NG-28 peroxidase conjugate gave a reading >1 on the plate coated with *N. gonorrhoeae* strains and <0.12 on that coated with *N. meningitidis* strains. At 1/16000 dilution of conjugate the optical densities were >1 on all the *N. gonorrhoeae* strains and <0.10 on all the *N. meningitidis* strains. Such readings were obtained for 22 different serotypes of *N. gonorrhoeae* and 8 serogroups of *N. meningitidis* including 11 serotypes of group B, i.e. readings of high OD with *N. gonorrhoeae* and low OD with *N. meningitidis*. The strains examined in this way are listed in Table 1 below.

EXAMPLE 2

Preparation of the specific protein using the monoclonal antibody secreted by hybridoma NG28 coupled to Sepharose ®

Protein A-purified Ig from hybridoma NG28, the Ig being IgG, was dialysed against 100 mM sodium bicarbonate pH 8.2 containing 500 mM sodium chloride. Sepharose ® CN.Br (Pharmacia) (3 g) was suspended in HCl 0.1N for 15 min then washed with the same bicarbonate buffer and added to 6.8 ml of IgG from hybridoma NG28 at 3.2 mg/ml. The bottle containing the mixture was rotated on a blood mixer for 1 hour at room temperature, then overnight at 4° C. to couple antibody to Sepharose ®. Residual active sites were blocked overnight with 500 mM ethanolamine adjusted to pH 9.0 and then with bovine serum albumin 0.5% in 100 mM glycine buffered at pH 8.2 in 150 mM saline for 2 hours. The Sepharose ®-antibody suspension was washed on a Buchner funnel with 150 mM saline and then poured into a column and washed with 25 mM ammonium bicarbonate.

A single strain of *N. gonorrhoeae* was grown on a selective medium and harvested into 66 mM Na/KH$_2$PO$_4$ buffer pH 7.2 containing the detergent CHAPS 0.1% and adjusted to $OD^{1cm}_{600nm} = 1.0$. The extraction buffer was allowed to act overnight at 4° C. Then the

| GENUS | SPECIES | SEROGROUP | SEROTYPE | NO. TESTED | REACTIVITY WITH NG28 |
|---|---|---|---|---|---|
| *Neisseria* | *gonorrhoea* | 1A | 1 | 1 | + |
| " | " | 1A | 2 | 1 | + |
| " | " | 1A | 3 | 1 | + |
| " | " | 1A | 6 | 1 | + |
| " | " | 1A | 8 | 1 | + |
| " | " | 1A | 13 | 1 | + |
| " | " | 1A | unknown | 7 | + |
| " | " | 1B | 1 | 1 | + |
| " | " | 1B | 2 | 1 | + |
| " | " | 1B | 3 | 1 | + |
| " | " | 1B | 4 | 1 | + |
| " | " | 1B | 5 | 1 | + |
| " | " | 1B | 6 | 7 | + |
| " | " | 1B | 7 | 1 | + |
| " | " | 1B | 8 | 1 | + |
| " | " | 1B | 12 | 1 | + |
| " | " | 1B | 14 | 1 | + |
| " | " | 1B | 16 | 1 | + |
| " | " | 1B | 17 | 1 | + |
| " | " | 1B | 18 | 1 | + |
| " | " | 1B | 22 | 1 | + |
| " | " | 1B | 26 | 1 | + |
| " | " | 1B | 30 | 1 | + |
| " | " | 1B | unknown | 9 | + |
| *Neisseria* | *meningitidis* | A | unknown | 1 | − |
| " | " | B | unknown | 2 | − |
| " | " | B | 1 | 1 | − |
| " | " | B | 2,10 | 1 | − |
| " | " | B | 4 | 1 | − |
| " | " | B | 9 | 1 | − |
| " | " | B | 2,7 | 1 | − |
| " | " | B | 5 | 1 | − |
| " | " | B | 14 | 1 | − |
| " | " | B | 8(1,3) | 1 | − |
| " | " | B | 11 | 1 | − |
| " | " | B | 6 | 1 | − |
| " | " | B | 2 | 1 | − |
| " | " | C | unknown | 1 | − |
| " | " | Y | " | 2 | − |
| " | " | W135 | " | 3 | − |
| " | " | 29E | " | 2 | − |
| " | " | X | " | 2 | − |
| " | " | Z | " | 1 | − |
| " | " | non-groupable | " | 2 | − | suspension was successively filtered to 0.45 μm before application to the Sepharose®-NG 28 antibody column. 150 ml of extract was slowly pumped onto the column at 0.5 ml/min, then the column was washed with 25 mM ammonium bicarbonate overnight. The column was then eluted with 25 mM ammonium hydroxide and the material absorbing at 280 nm pooled and dialysed with two changes against 2l of 20 mM ammonium bicarbonate. The yield of the protein which bound to the monoclonal antibody NG28 was 11.5 ml with an $OD^{1cm}{}_{280nm}=0.04$.

EXAMPLE 3

Production of further monoclonal antibodies

The protein obtained in Example 2 was transferred to a dialysis bag, concentrated to an $OD^{1cm}{}_{280nm}=0.28$ using PEG 6000 and then dialysed against 20 mM phosphate buffered saline. Balb/C mice were immunised subcutaneously with 100 μl each of the protein suspension homogenised with an equal volume of Freund's Incomplete Adjuvant and left for one month. The mice were boosted with a further intravenous injection of the protein suspension and, after 3 days, splenocytes obtained from the mice were fused with Non-secreting O myeloma cells of Balb/C origin using PEG 1540.

The hybridomas thus obtained were screened as described in Example 1(b). N. gonorrhoeae specific hybridomas were selected according to Example 1(c). In this way six further hybridomas were obtained which produced monoclonal antibody specific for the same protein as that for which the monoclonal antibody secreted by hybridoma NG28 was specific.

EXAMPLE 4

Assay of material suspected of containing N. gonorrhoeae

A sweep of bacteria suspected of being N. gonorrhoeae from a primary culture plate was extracted into 66 mM sodium phosphate buffer pH 7.4 containing 0.1% CHAPS w/v. An aliquot of this bacterial extract (250 μl) was mixed with horseradish peroxidase-labelled IgG (10 μl, 1/100 dilution) from hybridoma NG28, a portion (200 μl) of the mixture brought into contact with a solid support to which polyvalent rabbit anti-N. gonorrhoeae capture antibody was covalently bound and incubation carried out at room temperature (5 mins). After washing, tetramethylbenzidine/$H_2O_2$ substrate (250 μl) was added. A blue colour developed in the case of a positive. No colour developed when the organisms tested were other than N. gonorrhoeae. Results obtained in Table 2 below:

TABLE 2

|  | Strain Number | $OD_{600\,nm}{}^{1\,cm}$ Suspension | Colour developed at 2 min |
|---|---|---|---|
| Neisseria gonorrhoeae | 62a | 0.65 | tr/1 |
| " | 56a | 0.58 | 2 |
| " | 4166 | 0.92 | 1 |
| " | 64a | 0.96 | 2 |
| " | 68a | 0.88 | 2 |
| " | 6031 | 0.54 | 1 |
| " | C | 0.62 | 1 |
| " | 23 | 0.61 | 1 |
| Neisseria meningitidis | B/6610 | 0.84 | Neg |
| " | W135/7132 | 1.30 | Neg |
| " | W135/7782 | 1.10 | Neg |
| " | A/6140 | 0.94 | Neg |
| " | C/5536 | 0.96 | Neg |
| " | Y/6613 | 1.10 | Neg |
| Mixture of Neisseria meningitidis 1 vol | B/6610 | 1.47 | 2 |
| + Neisseria gonorrhoeae 1 vol | 62a | 0.85 |  |

We claim:

1. A monoclonal antibody which is specific for N. gonorrhoeae, which does not cross-react with N. meningitidis and which specifically binds to a protein obtained from N. gonorrhoeae, said protein having a molecular weight of about 14 kD as determined by SDS-PAGE wherein said protein specifically binds to an antibody secreted by hybridoma NG 28 deposited as Hybridoma No. ECACC 89071901.

2. The monoclonal antibody according to claim 1, which is the antibody secreted by hybridoma NG 28 deposited as hybridoma No. ECACC 89071901.

3. An immortalized cell line which secretes monoclonal antibody according to claim 1.

4. A cell line according to claim 3, which is hybridoma NG 28 deposited as hybridoma No. ECACC 89071901.

* * * * *